United States Patent [19]

Lehman

[11] Patent Number: 4,948,248

[45] Date of Patent: Aug. 14, 1990

[54] BLOOD CONSTITUENT MEASURING DEVICE AND METHOD

[75] Inventor: Thomas F. Lehman, Broken Arrow, Okla.

[73] Assignee: Invivo Research Inc., Winter Park, Fla.

[21] Appl. No.: 449,154

[22] Filed: Dec. 15, 1989

Related U.S. Application Data

[63] Continuation of Ser. No. 223,231, Jul. 22, 1988, abandoned.

[51] Int. Cl.⁵ .............................................. G01N 33/48
[52] U.S. Cl. ........................................ 356/40; 356/41; 128/633
[58] Field of Search .................... 356/40, 41; 128/665, 128/664, 633

[56] References Cited

U.S. PATENT DOCUMENTS

| | | | |
|---|---|---|---|
| 4,350,441 | 9/1982 | Wienienski | 356/40 |
| 4,447,150 | 5/1984 | Heinemann | 356/41 |
| 4,502,786 | 3/1985 | Golias et al. | 356/40 |
| 4,745,279 | 5/1988 | Karkar et al. | 356/40 |
| 4,819,752 | 4/1989 | Zelin | 128/633 |

Primary Examiner—Léon Scott, Jr.

[57] ABSTRACT

A method and device are disclosed for the detection of the relative percentage of at least one light absorber in the blood stream of living tissue. The method and device are based upon the employment of a narrow band width amplifier and pulses of different wavelength light sources wherein the frequency of the pulses of the light sources are selected so that a large component of the signal falls within the frequency of the narrow band amplifier, so that there is reduced likelyhood of interference from extraneous electromagnetic waves.

4 Claims, 2 Drawing Sheets

4,948,248

BLOOD CONSTITUENT MEASURING DEVICE AND METHOD

FIELD OF THE INVENTION

This invention relates to a blood constituent measuring device and method, and more particularly, relates to a non-invasive device and method for determining concentration of constituents in the blood through measurement of the difference in the absorption of different wavelengths of light as they are passed through living tissue containing blood.

BACKGROUND OF THE INVENTION

As is known, one blood constituent measuring device is an oximeter uses a photoelectric photometer to measure the fraction of hemoglobin in the blood which is in the form of oxygenated Hb. This oxygenated Hb fraction is generally referred to as a percentage where the percentage value is used to referred to the oxygen saturation of the blood.

Various oximeter devices and methods have been developed in the past. Some examples are disclosed in U.S. Pat. Nos. 4,407,290; 4,265,554; 4,167,331; 4,086,915; and 3,998,550, the disclosures of which are incorporated herein by reference. While oximetry devices and/or methods have heretofore been suggested and/or utilized, none of these devices and/or methods have proven to be completely satisfactory, and improvements have therefore still been needed with respect to such devices and/or methods.

Many of the prior art devices and methods make use of a plurality of sequences of pulses of light of different wavelength. The amount of light transmitted through the tissue is detected by a photo cell which in turn emits an electrical signal which is amplified and saved for processing. In order to property separate the pulses in the stream of data the photocell amplifier must be able to quickly settle back to the initial measurement level between each pulse. In order to obtain settling time a relative broad band amplifier has been employed in the past. The use of the broad band amplifier has lead to some difficulties. The oximeters are often used in operating rooms in which there are a wide range of electromagnetic wave producing devices present which can result in signals which introduce interference signals which can cause the device to give improper results.

An object of the present invention is to provide a device which is less susceptible to being affected by extraneous electromagnetic waves that may be present.

Other aspects, objects, and advantages of the present invention will become apparent to those skilled in the art having had the benefit of the following disclosure and the accompanying drawings.

SUMMARY OF THE INVENTION

In accordance with the present invention there is provided a method and device based upon the use of a narrow band photodetector amplifier and modulation of the pulses of different wavelength light sources so as to be compatible with the narrow frequency of the narrow band amplifier.

BRIEF DESCRIPTION OF THE DRAWINGS

A preferred embodiment of the present invention is illustrated in FIGS. 1-5. This embodiment employs two light emitting diodes (LED's), one of which emits light consisting essentially of the red wavelength and the other of which emits light consisting essentially of the infrared wavelength.

DETAILED DESCRIPTION OF THE INVENTION

Figure 1:
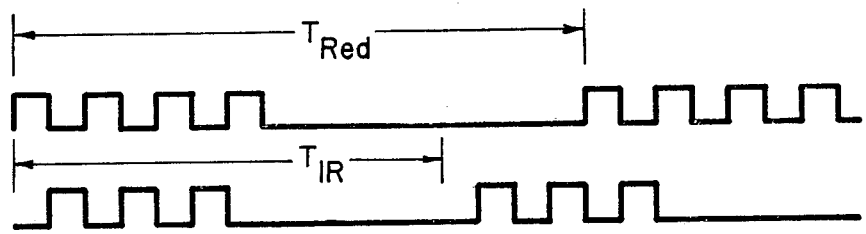

FIG. 1 shows a diagrammatical representation of the modulation of the light pulses over time. It will be noted that the red light is pulsed in sequences of four pulses spaced apart by a time period greater than the time period between the individual pulses in each sequence. The infrared light is similarly provided in a sequence of pulses separated by a longer time period.

The frequency spectra of the red channel has a fundamental frequency; of 1/TRED. Although higher harmonics do exist the primary part of the return signal is in that fundamental. Hence the receiving photocell amplifier can be tuned to the frequency or visa versa so that other electromagnetic waves present will not interfere with the analysis of the light absorption.

By shifting the phase of the sequences of pulses of the Infrared relative to that of the red light and by reducing the number of pulses of Infrared light in each sequence to number less than that of the number of pulses in the sequences of the red light, a different fundamental frequency can be achieved for the infrared light. The fundamental frequency of this second channel is 1/TIR.

Figure 2:
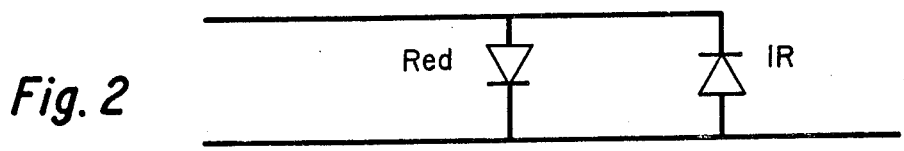

The use of the phase shift and the differing number of multiple pulses in the sequences allows to a read and infrared LED's to be connected back to back as shown in FIG. 2. This reduces the number of wires going to the sensing probe which in turn makes the probe lighter and more comfortable for a patient.

Figure 3:
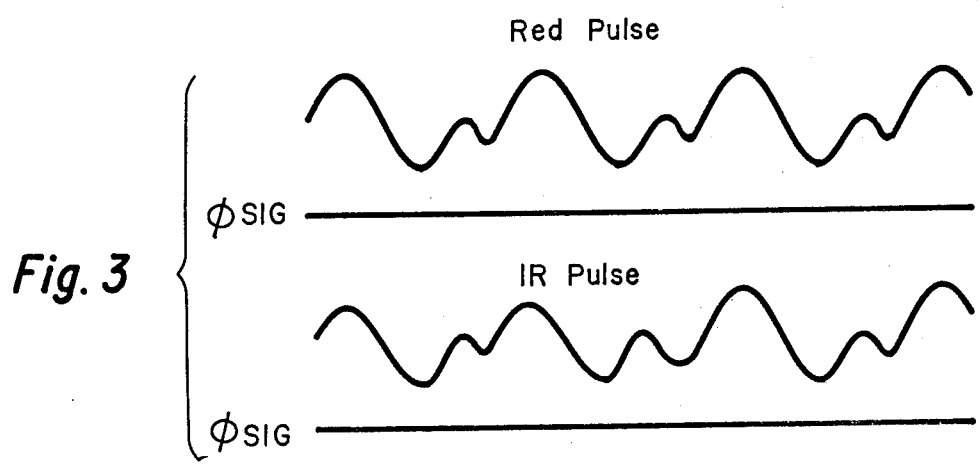
Figure 4:
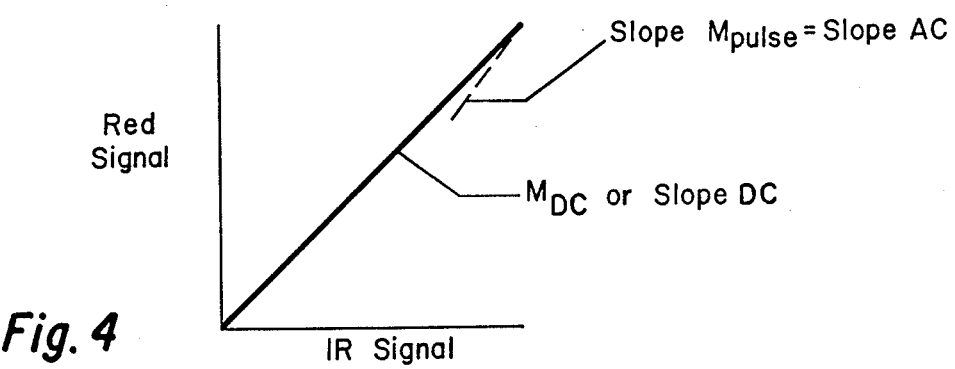

FIG. 3 shows an exaggerated represented of the returned signals from the sensor after appropriate rectification and filtering by the electronics. Each signal is made up of a large offset with a weak pulse ripple on the top. If the Red signal is plotted against the IR signal as shown in FIG. 4 a small diagonal line is traced on the graph. The slope of this line varies with the oxygen saturation, i.e. SaO2% concentration, of the blood. This slope will be referred to as the AC slope. If one then draws a line from the free end of the line of the AC slope to the ordinate of the graph one obtains another line. The slope of this line is referred to as the DC slope segment. The ration of the AC slope to the DC slope is related to the SaO2 concentration of the blood.

Figure 5:
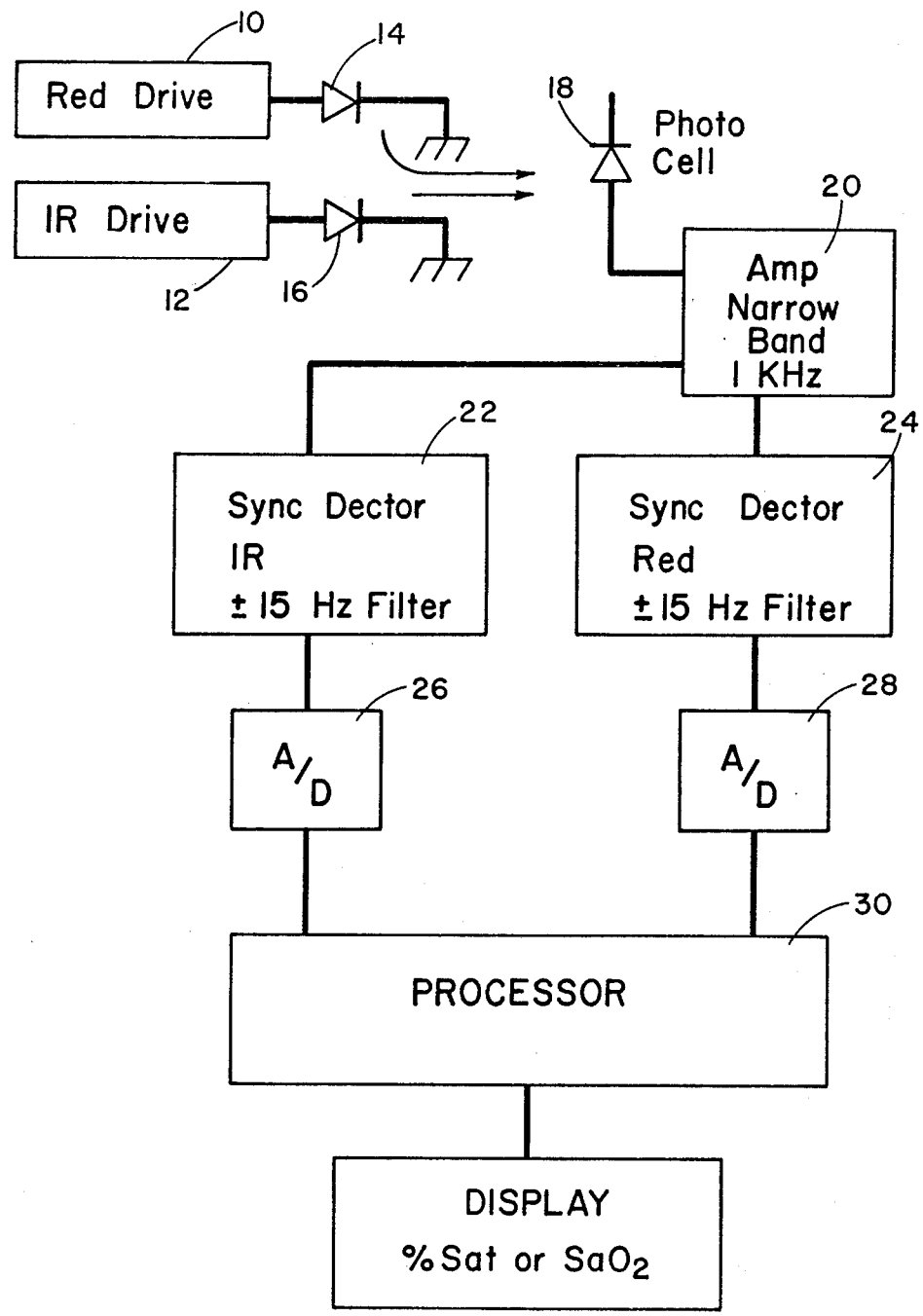

FIG. 5 is a block schematic diagram of an oximeter within the scope of the present invention. Shown are modulator drivers 10 and 12 for the re and infrared LED's 14 and 16. A photocell 18 is provided for use as is known in the art. Preferably this photocell is surrounded by a shield which will protect it from receiving extraneous electromagnetic emissions while at the same time allow the photocell to respond to the pulses of red and infrared light. The photocell 18 is connected to a narrow band 1 kHz amplifier 20, which in turn is connected to a synchronized IR detector 22 and a synchronized red light detector 24. The signals from those two selectors are passed to analog to digital converters 26 and 28. The IR detector is tuned to 1/TIR+or −15 Hz. The red light detector is tuned to 1/TRED+ or −15 Hz. The resulting digital values in turn can be processed in a microprocessor 30, or the like, to allow for the calculation of the percent oxygen saturation from the values obtained.

While the present invention has now been illustrated in regard to a preferred embodiment it should be noted that various modifications and variations can be made without departing from the spirit and scope of the present invention.

What is claimed:

1. A method of detecting the oxygen saturation in the blood of living tissue, comprising:
   (a) sequentially passing light of red frequency through the living tissue;
   (b) sequentially passing light of infrared frequency through the living tissue;
   (c) detecting the amplitude of light of red frequency transmitted through the tissue and providing electrical signals in response to such amplitude;
   (d) detecting the amplitude of light of infrared frequency transmitted through the tissue providing electrical signals in response to such amplitude; and
   (e) instantaneously and electronically platting said red light produced electrical signals against said infrared light produced electrical signals to obtain an output signal responsive to a slope of such plotted signals such that said slope is an indication of the oxygen saturation of blood in the tissue.

2. The method of detecting the oxygen saturation in the blood in living tissue according to claim 1 including the steps of;
   (f) converting the slope detected in step (e) to a numerical value indicating the percent of oxygen saturation of blood in the living tissue; and
   (g) displaying the numerical value from step (f).

3. The method of detecting the oxygen saturation in the blood in living tissue according to claim 1, wherein step (e) includes converting each of said red light and infrared light produced electrical signals into digital signals and plotting the red light digital signals against the infrared light digital signals in a microprocessor to provide said digital slope signal.

4. The method of detecting the oxygen saturation in the blood of living tissue according to claim 1 wherein step (a) of sequentially passing infrared light through the living tissue is 180 degrees out of phase with step (b) of sequentially red light through the living tissue.

* * * * *

UNITED STATES PATENT AND TRADEMARK OFFICE
CERTIFICATE OF CORRECTION

PATENT NO. : 4,948,248

DATED : Aug. 14, 1990

INVENTOR(S) : Lehman

It is certified that error appears in the above-identified patent and that said Letters Patent is hereby corrected as shown below:

Column 1, line 65, before "A" insert --Figure 1 is a graph showing diagrammatically the modulation of two light pulses over time.

Figure 2 is a circuit diagram showing the red and infrared LED's connected back to back.

Figure 3 is a graph showing the return signals from the red and infrared sensors.

Figure 4 is a plot of the red signal against the infrared signal.

Figure 5 is a block schematic diagram of an oximeter of the present disclosure.--

Signed and Sealed this

Fourth Day of February, 1992

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,948,248
DATED : Aug. 14, 1990
INVENTOR(S) : Thomas F. Lehman

It is certified that error appears in the above—identified patent and that said Letters Patent is hereby corrected as shown below:

```
Column 3, line 19, change "platting" to --plotting--.
Column 4, line 21, after "sequentially" add --passing--.
```

Signed and Sealed this

Eighth Day of December, 1992

*Attest:*

DOUGLAS B. COMER

*Attesting Officer*      *Acting Commissioner of Patents and Trademarks*